United States Patent [19]

Yamada et al.

[11] Patent Number: 5,228,975
[45] Date of Patent: Jul. 20, 1993

[54] GAS SENSOR HAVING HERMETIC AND ELECTRICALLY INSULATING SEAL IN HOUSING

[75] Inventors: Tatsuya Yamada; Toshiya Koide; Yoshihide Kami, all of Aichi, Japan

[73] Assignee: NGK Spark Plug Co., Ltd., Nagoya, Japan

[21] Appl. No.: 598,018

[22] Filed: Oct. 11, 1990

[30] Foreign Application Priority Data

Nov. 25, 1989 [JP] Japan .................. 1-306251

[51] Int. Cl.$^5$ ........................... G01N 27/416
[52] U.S. Cl. .................... 204/424; 204/421; 422/98
[58] Field of Search .............. 204/421–429, 204/153.18; 422/98

[56] References Cited

U.S. PATENT DOCUMENTS

| | | | |
|---|---|---|---|
| 3,914,169 | 10/1975 | Horowitz | 204/153.18 |
| 4,310,402 | 1/1982 | Isenberg et al. | 204/426 |
| 4,571,285 | 2/1986 | Nakazawa et al. | 204/153.18 |
| 4,624,770 | 11/1986 | Yamada et al. | 204/428 |
| 4,802,369 | 2/1989 | Morii | 204/424 |

FOREIGN PATENT DOCUMENTS 60-211345 10/1985 Japan .
63-154959 6/1988 Japan ........................... 204/426
1081545 8/1967 United Kingdom .............. 204/424

*Primary Examiner*—T. Tung
*Attorney, Agent, or Firm*—Foley & Lardner

[57] ABSTRACT

The invention relates to a gas sensor using a known gas sensitive element which provides an electrical output signal. For example, the sensitive element has a zirconia solid electrolyte sensitive to oxygen. The gas sensitive element is mounted on a ceramic substrate, and the substrate is partly inserted in a tubular housing, and a hermetic and electrically insulating seal column is formed in the housing to tightly hold the substrate. Lead wires protruding from the substrate are connected to external leads within the housing, and the joints are buried in the seal column. According to the invention, the seal column is formed of a glass-ceramic origitated from a glass which is composed of ZnO, $B_2O_3$, $SiO_2$ and MgO and has a crystallizing temperature of 740°–900° C. The glass-ceramic has a linear expansion coefficient smaller than that of the housing by $3 \times 10^{-6}$/°C. at the most. Preferably alumina ceramic is used as the housing material. The glass-ceramic seal column is high in heat resistance and remains sufficiently airtight and electrically insulating even when its temperature exceeds 500° C.

4 Claims, 3 Drawing Sheets

GAS SENSOR HAVING HERMETIC AND ELECTRICALLY INSULATING SEAL IN HOUSING

BACKGROUND OF THE INVENTION

This invention relates to a gas sensor having a gas sensitive element which is disposed in a housing and provides an electrical output signal indicative of the existence of a specific gas or the concentration of that gas in an environmental gas atmosphere, and more particularly to a hermetic and electrically insulating seal in the housing of the gas sensor.

There are various gas sensors using a semiconductive ceramic or a solid electrolyte ceramic as the principal material of the gas sensitive element. In such gas sensors usually the gas sensitive element is constructed on a ceramic substrate by a thin-film technique or a thick-film technique, and thin lead wires are connected to the gas sensitive element and fixed to the substrate. The lead wires protrude from the substrate at one end of the substrate. Usually the substrate is partly inserted in a tubular housing, and in the housing the lead wires protruding from the substrate are respectively connected to external leads or electrode pins. The substrate is held spaced from the inner wall of the housing by a suitable fixture, and the remaining space in the housing is filled with a sealant which provides an airtight and electrically insulating seal column. Consequently, an end portion of the ceramic substrate, lead wires protruding from the substrate and end portions of the external leads or pins are buried in the seal column.

Regarding the aforementioned seal column, JP-A 60-211345 recommends to use a glass, and particularly a lead borate glass, as the sealant. The seal column of a lead borate glass is good in airtightness and electrical insulation.

However, when the lead borate glass seal is employed restrictions are placed on the use of the gas sensor at high temperatures because the glass is relatively low in melting temperature and hence insufficient in insulation resistance at high temperatures. A lead borate glass contains at least 50 wt % of PbO and has a melting temperature ranging from about 500° C. to about 650° C. Therefore, the gas sensor must be used on condition that the temperature of the glass seal column in the sensor does not exceed about 400° C.

For many purposes it is desired to use gas sensors at considerably high temperatures, even at temperatures above 500° C. A good example is the use of an oxygen sensor in the exhaust system of an automotive internal combustion engine to provide a feedback signal indicative of the concentration of oxygen in the exhaust gas for controlling the air/fuel ratio of a combustible mixture to be fed to the engine. To enhance the precision of the air/fuel ratio control it is desirable to position the oxygen sensor at a very short distance from a combustion chamber. Then the temperature of the aforementioned seal column in the oxygen sensor will become higher than 500° C., and in the case of a lead borate glass seal the glass will soften and hence will become considerably low in insulation resistance. The lowering of the insulation resistance results in a leak of current between the lead wires buried in the glass seal column, and the leak of current is obstructive to accurate detection of the true output of the oxygen sensor, and hence the desire of enhancing the precision of the air/fuel ratio control cannot be met.

Besides, attention should be paid to the thermal expansion coefficient of the aforementioned seal column. For example, a lead borate glass has a linear expansion coefficient of about $7 \times 10^{-6}/°C$., whereas a stainless steel which is often used as the material of the aforementioned housing has a linear expansion coefficient of about $11 \times 10^{-6}/°C$. If there is such a difference in thermal expansion between the glass seal and the housing in direct contact with the glass seal, considerable thermal stresses are induced in the glass seal while the gas sensor is repeatedly heated and cooled in practical operations, and consequently cracks will appear in the glass seal column. Cracks in the seal column is unfavorable for insulation resistance and, besides, causes a leak of the sample gas such as the exhaust gas of a combustion engine through the gas sensor.

SUMMARY OF THE INVENTION

It is an object of the present invention to provide a gas sensor in which a ceramic substrate supporting thereon a gas sensitive element is partly inserted and tightly held in a housing by a hermetic, electrically insulating and sufficiently heat-resistant sealant.

The present invention relates to a gas sensor including a housing having a through-hole, a ceramic substrate which is partly inserted in the through-hole of the housing, a gas sensitive element which is provided on the ceramic substrate in a region protruding from the housing and provides an electrical signal indicative of the existence of or the concentration of a specific gas in an environmental gas atmosphere, and a hermetic and electrically insulating seal column which is formed in the through-hole of the housing so as to tightly fill a space between the ceramic substrate and the inner wall surface of the housing. According to the invention the hermetic and electrically insulating seal column is formed of a glass-ceramic originated from a glass which is essentially consisting of $ZnO$, $B_2O_3$, $SiO_2$ and $MgO$ and has a crystallizing temperature in the range from 750° to 900° C., the glass-ceramic having a linear expansion coefficient smaller than the linear expansion coefficient of the housing by $3 \times 10^{-6}/°C$. at the most.

It is preferred that the difference in linear expansion coefficient between the housing and the glass-ceramic is not more than $2 \times 10^{-6}/°C$.

In this invention it is preferred to employ an alumina ceramic as the material of the housing in which the glass-ceramic seal column is formed. The linear expansion coefficient of an alumina ceramic ranges from $6 \times 10^{-6}/°C$. to $8 \times 10^{-6}/°C$., and the linear expansion coefficient of a glass-ceramic employed in this invention can easily be controlled over the range from $4.7 \times 10^{-6}/°C$. to $5.3 \times 10^{-6}/°C$. Accordingly it is easy to establish a desired difference in thermal expansion between the housing and the glass-ceramic seal. Besides, an alumina housing is excellent in heat resistance and also in compatibility with the glass-ceramic.

Usually a gas sensitive element used in this invention are provided with lead wires which protrude from the ceramic substrate, and in the aforementioned housing the lead wires are respectively connected to external leads or electrode pins by soldering or welding. Preferably the glass-ceramic seal column according to the invention is formed such that the lead wires protruding from the ceramic substrate and end portions of the external leads or electrode pins including the joints with the respective lead wires are buried in the glass-ceramic column. By doing so both the lead wires and the glass-ceramic column become very tough and durable.

In the present invention the gas sensitive element is chosen from known gas sensitive elements, and there is no particular restriction on the type and structure of the gas sensitive element. For example, in the case of an oxygen sensor the principal material of the gas sensitive element may be a transition metal oxide such as $SnO_2$ or $TiO_2$ or an oxygen ion conductive solid electrolyte such as $ZrO_2$ containing a stabilizing oxide. According to the need the gas sensitive element may include a heater element.

In a gas sensor according to the invention the ceramic substrate supporting the gas sensitive element or an end part of the gas sensitive element is firmly and hermetically held in the housing by the glass-ceramic seal column, and the thermal expansion coefficient of the employed glass-ceramic is only slightly smaller than that of the housing material. Even though the sensor is repeatedly heated to high temperatures and cooled it is rarely that strong thermal stresses are induced in the glass-ceramic column since the glass-ceramic column and the housing expand and shrink nearly equally. Therefore, the glass ceramic column hardly cracks.

The glass-ceramic used in this invention is formed by partial crystallization of the specified glass at a considerably high temperature, i.e. at 750°–900° C. Therefore, this glass-ceramic is high in heat resistance and retains airtightness and a good insulating property even at temperatures higher than 500° C. Accordingly the gas sensor is fully practicable at high temperatures. Even though the sensor is used at temperatures close to 600° C. the glass-ceramic column in the sensor does not soften and does not deteriorate in airtightness, and the electrical insulation by the glass-ceramic is still sufficiently high so that the insulation resistance between the lead wires buried in the glass-ceramic column remains above $1M\Omega$ which is regarded as the minimum value for carrying out accurate measurement with the gas sensor.

It is preferable that the linear expansion coefficient of the glass-ceramic in the present invention falls in the range from $4.7\times10^{-6}/°C.$ to $5.3\times10^{-6}/°C.$, and a linear expansion coefficient in this range can be realized by using a glass composition consisting of 55–60 wt % of ZnO, 20–30 wt % of $B_2O_3$, 5–15 wt % of $SiO_2$ and 2–8 wt % of MgO (100 wt % in total).

DESCRIPTION OF THE PREFERRED EMBODIMENTS

Figure 1:
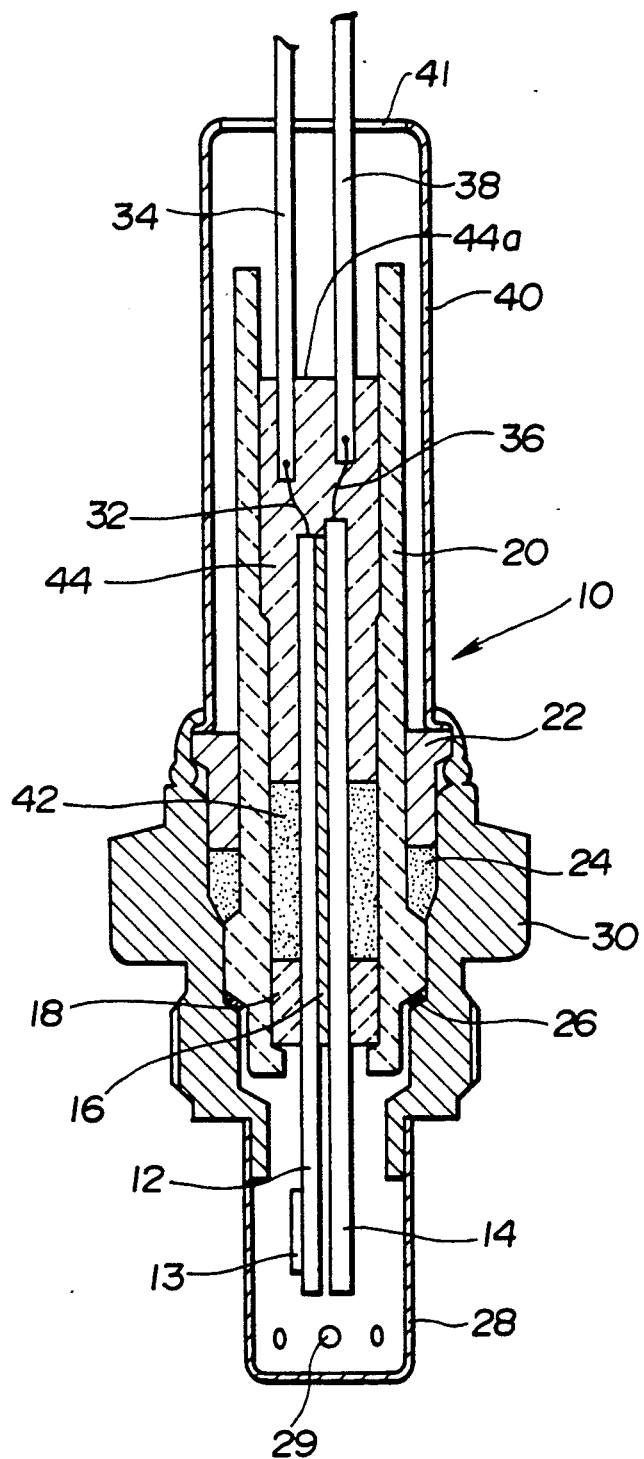
FIG. 1 is a longitudinal sectional view of a gas sensor embodying the present invention.

As an embodiment of the invention, FIG. 1 shows an oxygen sensor 10 for use in an exhaust system of an automotive internal combustion engine as an air/fuel ratio detector. Numeral 12 indicates a ceramic substrate, and the functional part of this oxygen sensor 10 is an oxygen sensor element 13 which is mounted on an end region of the substrate 12. For example, the oxygen sensor element 13 has a $SnO_2$, $TiO_2$ or $ZrO_2-Y_2O_3$ layer on which electrode layers are provided. Alternatively, a part of the gas sensor element may serve as the substrate 12. For example, in the case of an oxygen sensor element having a $ZrO_2-Y_2O_3$ solid electrolyte layer in the form of a plate, the solid electrolyte plate (which is a ceramic plate) may be designed so as to serve as a structurally basic part of the sensor element. In such a case the ceramic substrate 12 in FIG. 1 refers to the solid electrolyte plate. To keep the oxygen sensor element 13 heated in operating the sensor 10 a heater 14 is bonded to the ceramic substrate 12 with a ceramic cement 16. In this case the heater 14 is a thin plate of a ceramic such as an alumina ceramic provided with heater elements (not shown). Alternatively, heater elements may be provided to the ceramic substrate 12 without using the illustrated plate.

The assembly of the substrate 12 and the heater 14 is partly fitted in an inner tube (housing) 20 and fixed to the tube 20 by using a perforated ceramic ring 18 such that an end portion of the assembly including the oxygen sensor element 13 protrudes from the tube 20. Preferably the inner tube 20 is made of an alumina ceramic. The inner tube 20 is fitted in a metal shell 30 for attachment of the sensor 10 to the exhaust manifold or exhaust pipe of the engine. The tube 20 is fixed to the metal shell by using an annular spacer 22, an inorganic cement 24 and a leaf packing 26. A protective cap 28 formed with gas admitting holes 29 is attached to a forward end of the metal shell 30 so as to encapsulate the protruding portion of the substrate 12 together with the heater 14. An outer tube 40 is attached to the rear end of the metal shell 30 so as to cover a rear section of the inner tube 20 protruding from the metal shell 30.

In the inner tube 20, each of lead wires 32 which extend from the oxygen sensor element 13 and protrude from the substrate 12 is welded to an electrode pin (or wire) 34, and each of lead wires 36 extending from the heater 14 is welded to an electrode pin (or wire) 38. The electrode pins 34, 38 extend through an opening 41 at the rear end of the outer tube 40. For example, the lead wires 34, 36 are platinum wires, and the electrode pins 36, 38 are made of copper or a stainless steel.

In the inner tube 20, a forward section contiguous to the fixing ring 18 is packed with an inorganic powdery sealant 42 such as a powder mixture of talc and/or alumina and a glass, and the remaining rear section in which the lead wires 32 and 36 are connected to the electrode pins 34 and 38, respectively, is filled with a glass-ceramic 44. Also it is possible to fill almost the entire space in the inner tube 20 with the glass-ceramic 44 by omitting the powdery sealant 42. The glass-ceramic 44 originates from a glass composition which is composed of ZnO, $B_2O_3$, $SiO_2$ and MgO and has a crystallizing temperature in the range from 750°–900° C., and the glass composition is adjusted such that the linear expansion coefficient of the glass-ceramic 44 is lower than the linear expansion coefficient of the inner tube 20 by $3 \times 10^{-6}/°C$. at the most and preferably not more than $2 \times 10^{-6}/°C$.

EXAMPLE

An oxygen sensor of the construction shown in FIG. 1 was produced in the following way.

The inner tube 20 was an alumina ceramic tube, which was obtained by sintering a green body at about 1600° C. The alumina tube 20 had a thermal expansion coefficient of about $7 \times 10^{-6}/°C$.

The lead wires 32 and 36 were connected to the electrode pins 34 and 38, respectively, by spot welding. After that the assembly of the ceramic substrate 12 supporting the oxygen sensor element 13 and the heater 14 was partly inserted into the inner tube 20 together with the fixing ring 18. Next, the glass-ceramic column 44 was formed by the following process. In this example the column of the powdery sealant 42 was omitted so that the glass-ceramic column 44 was in contact with the fixing ring 18.

A glass composition was prepared by mixing 60 wt % of ZnO, 25 wt % of $B_2O_3$, 10 wt % of $SiO_2$ and 5 wt % of MgO, and pulverizing the mixture so as to obtain a mixed powder having a mean particle size of about 150 μm. The mixed powder was packed in the rear section of the inner tube 20 such that the end portions of the plates 12 and 14, the protruding lead wires 32, 36 and end portions of the electrode pins 34, 38 were buried in the mixed powder. Then the inner tube 20 was baked at about 800° C. for 1 hr in order to melt the powder of the glass composition and precipitate crystals from the molten glass. By this treatment the packed column of the glass composition powder turned into a glass-ceramic column 44. The glass-ceramic 44 had a linear expansion coefficient of $5 \times 10^{-6}/°C$., which was smaller than that of the ceramic inner tube 20 by about $2 \times 10^{-6}/°C$. In this oxygen sensor the glass-ceramic seal column 44 was formed in such a length that the spot-welded joint of each lead wire 32, 36 with the corresponding electrode pin 34, 38 was at a considerable depth from the exposed end 44a of the seal column 44. That is, a considerable length of each electrode pin 34, 38 was firmly inserted into the glass-ceramic column 44. This arrangement is effective for preventing peel of the spot-welded joints and firmly holding the lead wires and the electrode pins.

Next, the inner tube 20 was fitted in the metal shell 30 by precedingly placing the leaf packing 26 on the tapered shoulder of the inner wall of the shell 30 to enhance airtightness. Then the inorganic cement layer 24 was formed by using a mixture of talc powder and about 5 wt % of water glass, and the annular spacer 22 made of stainless steel was inserted to thereby complete airtight fitting of the inner tube 20 in the metal shell 30. Then the outer tube 40 was fixed to the metal shell 30. The protective cap 28 was attached to the metal shell 30 in advance. The opening 41 of the outer tube 40 was closed by a rubber plug and a protective metal cap (not illustrated).

Several samples of the oxygen sensor 10 were produced under the same conditions.

COMPARATIVE EXAMPLE 1

The oxygen sensor 10 of the above Example was modified only in the following two points.

First, the material of the inner tube 20 was changed to a stainless steel having a linear expansion coefficient of about $11 \times 10^{-6}/°C$.

Second, the glass-ceramic column 44 in the Example was replaced by a column of a lead borate glass containing about 60 wt % of PbO. This lead borate glass had a melting temperature of about 650° C. and a linear expansion coefficient of $7 \times 10^{-6}/°C$., and this glass was not crystallizing.

COMPARATIVE EXAMPLE 2

The oxygen sensor of Comparative Example 1 was modified only in the particulars of the lead borate glass used in the seal column 44. In this case the lead borate glass contained about 75 wt % of PbO and had a melting temperature of about 500° C. and a linear expansion coefficient of $8.5 \times 10^{-6}/°C$. This glass was not crystallizing.

Samples of the oxygens sensors of the Example and Comparative Examples 1 and 2 were subjected to the following evaluation tests.

EVALUATION TEST 1: Insulation Test

Figure 2:
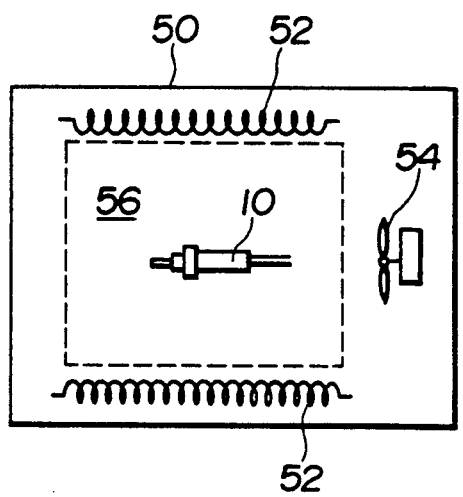
FIG. 2 is a schematic and sectional illustration of an electric furnace used in testing a gas sensor according to the invention.
Figure 3:
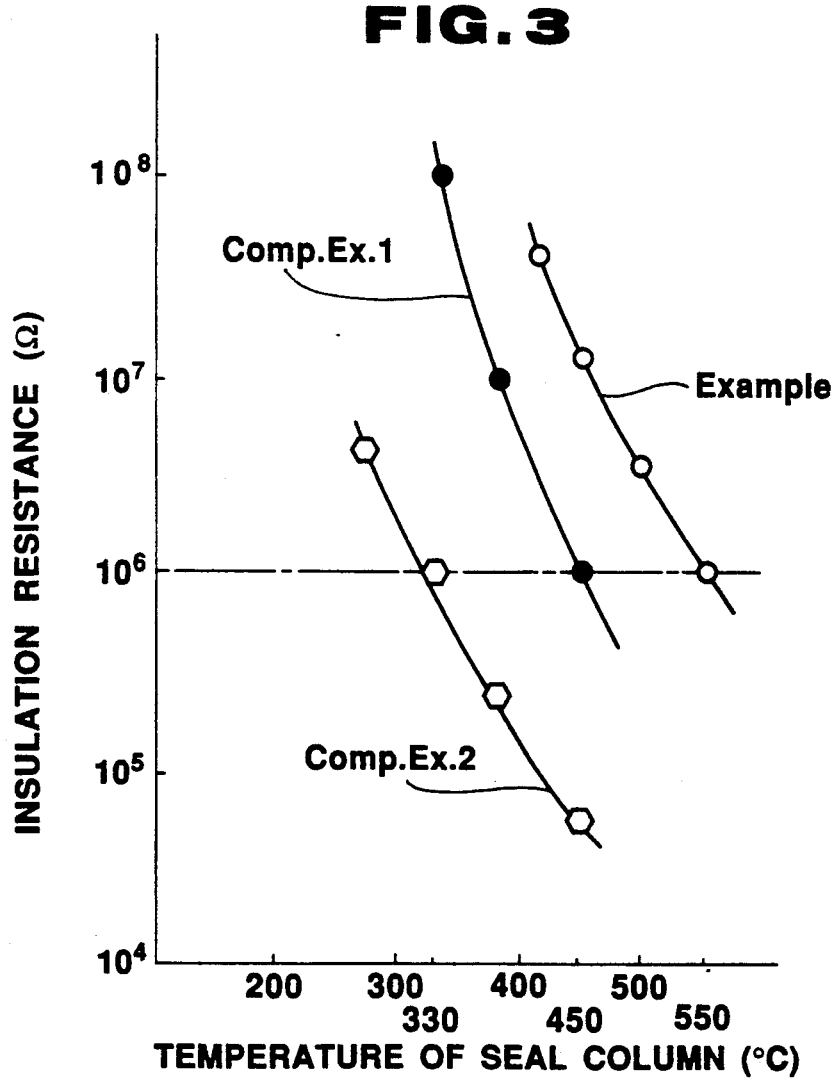
FIG. 3 is a graph showing the results of an electrical insulation test made at elevated temperatures on a gas sensor according to the invention and comparative gas sensors not in accordance with the invention.

Referring to FIG. 2, the test was made in an electric furnace 50 having heaters 52 and a fan 54. Each oxygen sensor 10 was placed in a thermostatic chamber 56 in the furnace 50, and the insulation resistance of the sensor 10 was measured at various temperatures by applhing a DC voltage of 50 V between the electrode pins 34 and 38. The temperatures in the thermostatic chamber 56 were measured by a thermocouple (not shown), and the temperatures of the glass-ceramic or glass column 44 in the sensor 10 were deduced from the measured temperatures based on a calibration curve obtained in advance. The results are shown in FIG. 3.

In the oxygen sensor 10 the insulation resistance between the electrode pins 34 and 38 should not be lower than $1M\Omega$ for accurately outputting the current or voltage signal representative of the function of the oxygen sensitive element. As can be seen in FIG. 3, in the sensor 10 of Comparative Example 2 using the lead borate glass low in melting temperature the insulation resistance became lower than $1M\Omega$ ($10^6\Omega$) as the temperature of the glass seal column 44 rose to 330° C. or above. In the sensor 10 of Comparative Example 1 using the lead borate glass medium in melting temperature the insulation resistance became lower than $1M\Omega$ as the temperature rose to 450° C. or above. In the sensor 10 of Example using the glass-ceramic the insulation resistance was higher than $1M\Omega$ until the temperature of the glass-ceramic column 44 reached 550° C.

EVALUATION TEST 2: Airtightness Test

Figure 4:
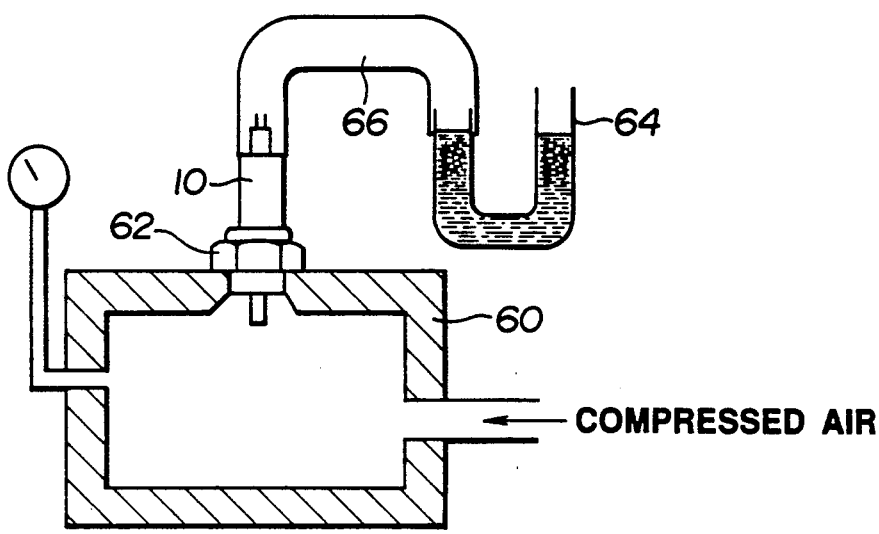
FIG. 4 is a schematic and sectional illustration of a leak detecting apparatus used in testing samples of a gas sensor according to the invention and comparative gas sensors.

Using the electric furnace 50 of FIG. 2, each oxygen sensor 10 was stored in the thermostatic chamber 56 maintained at a predetermined temperature which has 450° C., 500° C., 600° C., 650° C. or 700° C. After the lapse of a predetermined period of time the sensor 10 was taken out of the furnace 50 and subjected to a leak test by using the apparatus shown in FIG. 4. Numeral 60 indicates a pressure chamber using compressed air. The oxygen sensor 10 was fitted in a hole in the wall of the pressure chamber 60 such that the protective cap 28 of the sensor 10 intruded in the chamber 60, and the sensor 10 was airtightly fixed by a fixture 62. The rear end (outer tube 40) of the sensor 10 was connected to a leg of a U-tube manometer 64 (using mercury or water) by a pipe 66. The other leg of the manometer 64 was left open to the atmosphere at room temperature, and the pressure in the chamber 60 was maintained at 15 kg/cm². If there was a leak of air from the pressure chamber 60 to the U-tube manometer 64 through the tested sensor 10 the leak could be detected, and the rate of the leak was measured. The test results are shown in FIG. 5.

Figure 5:
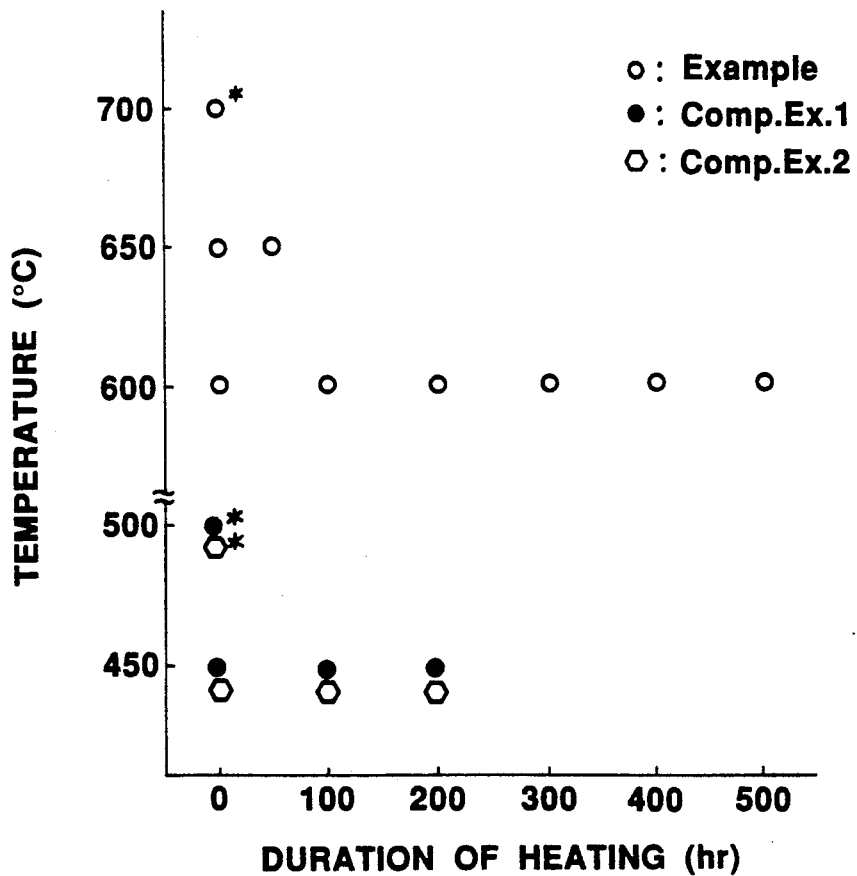
FIG. 5 is a graph showing the results of a high temperature endurance test on the gas sensor according to the invention and the comparative gas sensors with respect to airtightness of each sensor.

In FIG. 5, the asterisk (*) attached to a circle or hexagon mark indicates the occurrence of a leak of air through the tested sensor 10 at a rate of 1 cm$^3$/min or above. With respect to the sensors of Comparative Examples 1 and 2 using a lead borate glass, no leak of air was detected when the leak test was made after heating the sensors at 450° C. for up to 200 hr, but a leak of air occurred when the leak test was made after heating the sensors at 500° C. for only 0.5 to 5 hr. With respect to the sensors 10 of Example using the glass-ceramic, no leak of air was detected even when the leak test was made after heating the sensors at 600° C. for 500 hr or at 650° C. for 50 hr, though a leak of air occurred when the leak test was made after heating the sensors at 700° C. for 0.5 to 10 hr. Thus, the results of this test evidence that even at high temperatures extending to 600° C. the oxygen sensor 10 of the Example of the invention can be used for a long period of time without suffering from cracking of the glass-ceramic seal column 44 and without deteriorating in airtightness.

As evidenced by the results of the evaluation tests, gas sensors according to the invention can be used even at temperatures too high for using conventional gas sensors. In the case of an oxygen sensor according to the invention for use as an air/fuel ratio detector in the exhaust system of an internal combustion engine, it is possible to position the sensor at a shorter distance from an exhaust port than in the case of using a conventional oxygen sensor. Therefore, it becomes possible to measure the concentration of oxygen in the exahust gas immediately after combustion, and by using the so measured value as a feedback signal it is possible to enhance the precision of the control of the air/fuel ratio of a combustibel mixture to be fed to the engine. Even if the temperature of the glass-ceramic column 44 in the sensor rises to the extent of 500°-600° C. the output of the sensor is very accurate and reliable since the sensor still retains high insulation resistance and good airtightness, so that accurate detection of air/fuel ratio can be carried out.

What is claimed is:

1. In a gas sensor having a tubular metal shell, a tubular inner housing which is at least partly and substantially coaxially inserted into the metal shell, a ceramic substrate which is partly inserted in the bore of the inner housing, a gas sensitive element which is provided on the ceramic substrate in a region protruding from the inner housing and provides an electrical output signal indicative of the existence of or the concentration of a specific gas in an environmental gas atmosphere, at least one combination of a lead wire which is connected to the gas sensitive element and fixed to the ceramic substrate and protrudes from the ceramic substrate so as to extend in the bore of the inner housing and an elongate external lead member which is partly into the bore of the inner housing from an end remote from the ceramic substrate and connected to the lead wire, and a hermetic and electrically insulating seal column which tightly fills a section of the bore of the inner housing such that the lead wire protruding from the ceramic substrate and an end portion of the external lead member including the joint with the lead wire are buried in the seal column, the improvement comprising said seal column being formed of a glass-ceramic formed by heat treatment of a glass which consists essentially of ZnO, B$_2$O$_3$, SiO$_2$, and MgO and has a crystallizing temperature in the range from 750° to 900° C., said inner housing being made of a ceramic, said glass-ceramic having a linear expansion coefficient smaller than the linear expansion coefficient of said ceramic by not more than $3\times10^{-6}$/°C.

2. A gas sensor according to claim 1, wherein the difference between the linear expansion coefficient of said ceramic and the linear expansion coefficient of said glass-ceramic is not more than $2\times10^{-6}$/°C.

3. A gas sensor according to claim 1, wherein said glass-ceramic has a linear expansion coefficient in the range from $4.7\times10^{-6}$/°C. to $5.3\times10^{-6}$/°C.

4. A gas sensor according to claim 1, wherein said ceramic of said inner housing is an alumina ceramic.

* * * * *